United States Patent [19]

Croll

[11] Patent Number: 4,753,594
[45] Date of Patent: Jun. 28, 1988

[54] DENTAL HANDPIECE WITH ROTARY MANDREL

[76] Inventor: Theodore P. Croll, 685 S. Chubb Dr., Doylestown, Pa. 18901

[21] Appl. No.: 82,282

[22] Filed: Aug. 6, 1987

[51] Int. Cl.[4] .............................................. A61C 3/06
[52] U.S. Cl. .................................... 433/125; 433/166
[58] Field of Search ....................... 433/165, 166, 125

[56] References Cited

U.S. PATENT DOCUMENTS

| | | | |
|---|---|---|---|
| 1,617,838 | 2/1927 | Fennell | 433/127 |
| 3,309,772 | 3/1967 | Lieb et al. | 433/166 |
| 3,775,849 | 12/1973 | Condon | 433/125 |

*Primary Examiner*—Carroll B. Dority, Jr.
*Attorney, Agent, or Firm*—Gregory J. Gore

[57] ABSTRACT

An applicator system for a powered dental handpiece enables the low RPM controlled application of abrasive tooth compound. The system comprises, in combination, a speed reducer and a mandrel which includes a grooved cylindrical sleeve. The mandrel is made from substantially rigid material so that pressure may be applied to the tooth without deformation of the mandrel and, hence, increased contact surface area between the applicator sleeve and the tooth is prevented. The mandrel further includes a central containment pocket for holding and applying the tooth compound so that both inner and outer portions of the applicator sleeve are operable. A ring-shaped end portion of the applicator sleeve is effective for spot application of the compound.

4 Claims, 1 Drawing Sheet

DENTAL HANDPIECE WITH ROTARY MANDREL

FIELD OF THE INVENTION

This device relates to apparatus used in dentistry and, more specifically, a powered dental handpiece for intra-oral use.

BACKGROUND OF THE INVENTION

It is well-known in the art to use powered rotary instruments with special applicators for applying dental compounds to human teeth during various dental procedures. It is also well-known that the applicator mandrels which apply the compound to the tooth have different designs in order to facilitate their utility. One general design shown to be very effective is a rotary mandrel with a cup-like applicator tip extremely flexible sides and which has a central pocket to hold a quantity of compound against the tooth while it is being applied. Many of the commonly used tooth compounds are for superficial tooth cleaning only. Hence, in order to avoid abrasion of the tooth enamel, the rotary applicators often utilize extremely flexible applicator cups in order to minimize the pressure of the compound against the tooth. Using this low pressure with the high RPM capability of the standard dental handpiece yields very effective cleaning using a mild cleaning paste.

New compounds are presently being devised, however, for which the old application techniques and devices are no longer recommended. Such a compound is described in pending U.S. patent application Ser. No. 811,447 pending describing an extremely abrasive compound incorporating an enamel-dissolving acid. Normal methods of powered compound application have proven unsatisfactory using this new compound. The high RPM nature of the dental handpiece, together with the very flexible sidewall of the normal compound applicator cup, does not permit the required control of the enamel-shaping compound.

SUMMARY OF THE INVENTION

In order to overcome the disadvantages mentioned above with the standard powered application techniques, the present application system utilizes, in combination, a 10-to-1 speed reduction adaptor and a novel rotary mandrel tip. Using this system, enamel abrading compounds can be used with great controllability while permitting the dentist to perform the procedure in one-third of the time of manual application using a hand applicator stick.

A first part of this system includes a 10-to-1 speed reduction adaptor which drastically reduces the RPM of the rotating tip in order to make the application of the compound more controllable. There is some sacrifice in reducing abrasion because of the loss of RPM, however, such high RPM is not needed with the extremely abrasive compound and the added controllability has been found a net benefit in the trade off.

The second part of the application system is a rotary mandrel which has been specifically designed to operate at extremely low RPM in a manner which allows higher pressure and control over the compound as it is being applied against the tooth. This mandrel includes a tip portion which is substantially cylindrical in configuration and which includes a shallow well or containment pocket for the compound. The mandrel tip has some resilience in the material, however, it is substantially rigid as compared to other paste applicator cups which are made from a very flexible rubber. The mandrel tip further includes longitudinal striations creating frictional grooves along the outer surface of the tip so that both the inner and outer portions of the tip can be used to apply the compound. For spot application, the end axial surface of the mandrel in the shape of a ring at the end of the tip can be used effectively. The fact that the tip is made from more rigid material means that greater pressure can be applied against the tooth without deformation of the mandrel which would unduly increase the contact area.

Other advantages will become obvious to those of ordinary skill in the art from the following drawings and description of the preferred embodiment which follows.

DESCRIPTION OF THE PREFERRED EMBODIMENT

Figure 1:
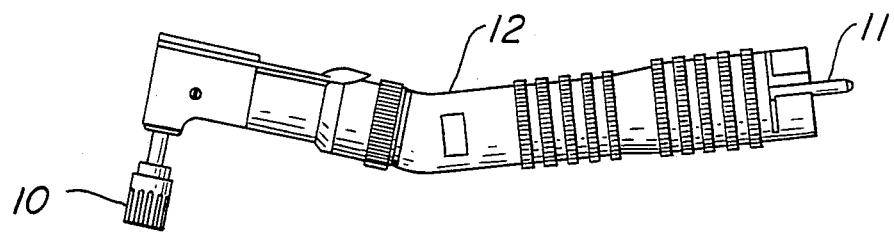
FIG. 1 shows an overall view of the speed reducer drive with the novel rotary mandrel inserted.
Figure 2:
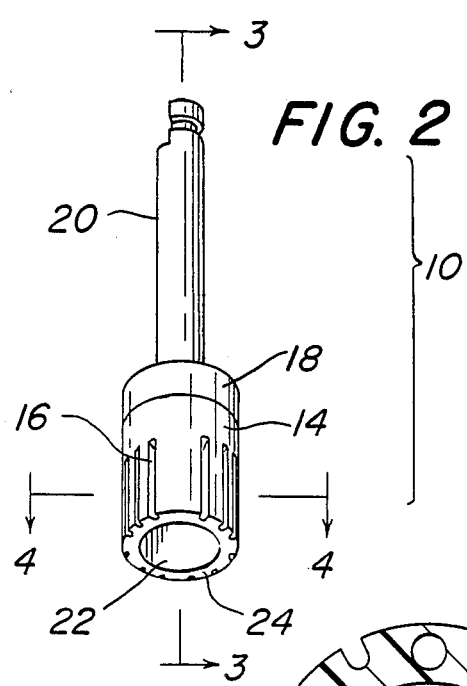
FIG. 2 is an isometric view of the rotary mandrel.

Referring now to FIG. 1, speed reducer drive 12 is shown with rotary mandrel 10 inserted therein. The drive contains shaft 11 for mounting in a standard dental handpiece (not shown). FIG. 2 is an isometric view of the rotary mandrel. Shank 20 is connected to base portion 18 containing sleeve 14 which applies the tooth compound. Sleeve 14 further includes friction grooves 16 which allow the outer circumference of the applicator sleeve to be also used for applying the tooth compound. Central containment cup 22 holds a quantity of compound to be applied and provides an inner surface of the applicator sleeve to be used for application of the tooth compound in curved areas of the tooth. In this way, both the inner and outer surfaces of applicator sleeve 14 are operative.

Figure 3:
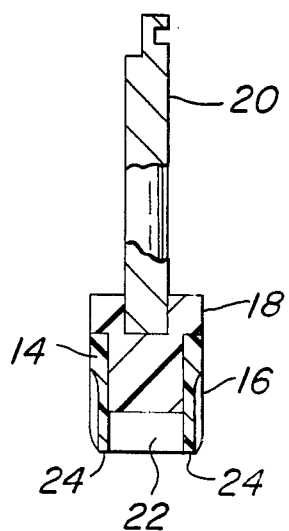
FIG. 3 is a longitudinal section of the rotary mandrel of FIG. 2.
Figure 4:
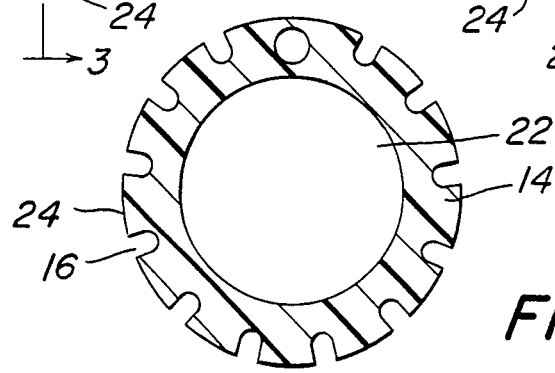
FIG. 4 is a transverse radial section taken from FIG. 2.

Referring now to FIG. 3, a more detailed construction of the rotary mandrel is shown. Shank 20 is affixed to base portion 18 which carries the applicator sleeve 14. Friction grooves 16 extend from the very tip of the mandrel back along most of the tip's circumference. Applicator sleeve 14 is longer than the axial length of base 18 creating a compound containment pocket 22 for transporting and applying a quantity of tooth compound. FIG. 4 shows greater detail of the construction of the applicator sleeve showing the friction groove 16 and a ring-shaped axial end surface 25 for applying compound.

It should be understood that the above description discloses specific embodiments of the present invention and are for purposes of illustration only. There may be other modifications and changes obvious to those of ordinary skill in the art which fall within the scope of the present invention which should be limited only by the following claims and their legal equivalents.

What is claimed is:

1. A device for the application of tooth-treatment compound in dentistry, comprising:
   a. a rotary applicator mandrel,
   b. a cylindrical outer sleeve portion of said mandrel adjacent a first end, c. a plurality of longitudinal grooves circumferentially spaced around the outer surface of said sleeve and extending to the extremity of said first end of said sleeve portion, d. a tooth compound pocket at said first end of said mandrel for retaining and applying a quantity of tooth compound, and e. said sleeve being made of substantially rigid material whereby high pressure application of said compound against said tooth may be achieved without substantially deforming said sleeve.

2. The dental device of claim 1 further including a rigid base portion which interconnects a shank to said applicator sleeve portion.

3. The device of claim 2 wherein said first end further including a ring-shaped axial end surface for application of said compound.

4. The device of claim 1 further including a speed reducer drive means having said mandrel inserted therein.

* * * * *